United States Patent
Kim et al.

(10) Patent No.: US 10,588,781 B2
(45) Date of Patent: Mar. 17, 2020

(54) OPHTHALMIC TREATMENT DEVICE

(71) Applicant: LUTRONIC VISION INC, Burlington, MA (US)

(72) Inventors: Jong Min Kim, Seoul (KR); Tae Ho Ha, Goyang (KR)

(73) Assignee: LUTRONIC VISION INC, Burlington, MA (US)

( * ) Notice: Subject to any disclaimer, the term of this patent is extended or adjusted under 35 U.S.C. 154(b) by 689 days.

(21) Appl. No.: 15/310,079

(22) PCT Filed: May 11, 2015

(86) PCT No.: PCT/KR2015/004702
§ 371 (c)(1),
(2) Date: Nov. 9, 2016

(87) PCT Pub. No.: WO2015/170947
PCT Pub. Date: Nov. 12, 2015

(65) Prior Publication Data
US 2017/0266041 A1    Sep. 21, 2017

(30) Foreign Application Priority Data
May 9, 2014   (KR) .................. 10-2014-0055671

(51) Int. Cl.
*A61F 9/008*    (2006.01)
*A61B 3/12*     (2006.01)
(Continued)

(52) U.S. Cl.
CPC ............ *A61F 9/008* (2013.01); *A61B 3/0008* (2013.01); *A61B 3/12* (2013.01); *A61B 90/37* (2016.02);
(Continued)

(58) Field of Classification Search
CPC ................. A61F 9/008; A61F 9/00821; A61F 2009/00863; A61F 2009/00897; A61B 3/0008; A61B 3/12
See application file for complete search history.

(56) References Cited

U.S. PATENT DOCUMENTS

2009/0093798 A1 *   4/2009   Charles ................. A61F 9/0079
                                                              606/4

FOREIGN PATENT DOCUMENTS

JP      2001-258853 A      9/2001
JP      2008-086412 A      4/2008
(Continued)

OTHER PUBLICATIONS

International Search Report for International Patent Application No. PCT/KR2015/004702 filed May 11, 2015.

*Primary Examiner* — Tammie K Marlen (57) ABSTRACT

The present invention relates to an ophthalmic treatment device and a method of operating same, and provides an ophthalmic treatment device and a method of operating same, the device comprising: a treatment beam generating unit for generating a treatment beam; a beam delivery unit for forming a path through which the treatment beam generated by the treatment beam generating unit travels to a treatment region disposed in a fundus; a monitoring unit for irradiating a detecting beam along the path through which the treatment beam travels, and detecting information of the state of the treatment region based on interference information on the detecting beam reflected from the treatment region; and a controller for controlling the operation of the treatment beam generating unit based on information on the state of the treatment region detected by the monitoring unit.

17 Claims, 8 Drawing Sheets

(51) Int. Cl.
   *A61B 3/00*      (2006.01)
   *A61B 90/00*     (2016.01)
   *A61B 90/30*     (2016.01)
(52) U.S. Cl.
   CPC .... *A61F 9/00821* (2013.01); *A61B 2090/309* (2016.02); *A61B 2090/3612* (2016.02); *A61B 2090/373* (2016.02); *A61F 2009/00863* (2013.01); *A61F 2009/00897* (2013.01)

(56) References Cited

FOREIGN PATENT DOCUMENTS

| | | |
|---|---|---|
| JP | 2013-116424 A | 6/2013 |
| KR | 10-2014-0009845 A | 1/2014 |
| KR | 10-2014-0009846 A | 1/2014 |
| WO | WO 2009/045286 A1 | 4/2009 |
| WO | WO 2014/049132 A1 | 4/2014 |

* cited by examiner

OPHTHALMIC TREATMENT DEVICE

CROSS-REFERENCE TO RELATED APPLICATIONS

The present specification is a U.S. National Stage of International Patent Application No. PCT/KR2015/004702 filed May 11, 2015, which claims priority to and the benefit of Korean Patent Application No. 10-2014-0055671 filed in the Korean Intellectual Property Office on May 9, 2014, the entire contents of which are incorporated herein by reference.

BACKGROUND OF THE INVENTION

Field of the Invention

The present disclosure relates to an ophthalmic treatment device and a method of operating the same, and more specifically to an ophthalmic treatment device, which enables a user to perform treatment while checking a treatment region of fundus, and a method of operating the same.

Related Art

Recently, a technology of irradiating a beam, which can be absorbed the in human body, and changing a state of tissues with light energy is widely used. In particular, treatment devices using laser are used for treatment of various kinds of lesions related to skin disorders, eye disorders, neurological disorders, joint disorders, gynecologic disorders, etc.

A number of ophthalmic treatment devices using laser have been developed, which are used for treatment of lesions in an anterior segment of eye, such as cornea modification, glaucoma surgery, cataract surgery, etc. These days, many efforts are made to develop devices for treatment of macular degeneration and other various fundus lesions. One of those devices is introduced by Korean Patent Application Publication No. 10-2014-0009846.

An existing ophthalmic treatment device utilizes lighting to enable a user to observe a retinal surface tissue which can be seen from the outside. However, it is not possible to obtain additional information on an internal tissue located at a predetermined depth below the surface, so it is difficult to check the treatment procedures or whether treatment is performed properly.

SUMMARY OF THE INVENTION

The present disclosure aims to provide an ophthalmic treatment device, which provides an image of an internal tissue of a diseased area so as to check a state of the internal tissue, and a method of operating the ophthalmic treatment device.

To achieve the above object, there is provided an ophthalmic treatment device including a treatment beam generating unit configured to generate a treatment beam, a beam delivery unit configured to form a path along which the treatment beam generated by the treatment beam generating unit travels to a treatment region in fundus, an image detecting unit configured to adjust a parameter of an imaging beam that is irradiated onto a tissue of the treatment region so as to acquire a fundus image including the tissue, and a display unit configured to display the fundus image, acquired by the image detecting unit, for a user.

The image detecting unit may select the parameter of the imaging beam based on depth of the tissue in the treatment region.

The image detecting unit may acquire a fundus image of tissues which are adjacent to a Retina Pigment Epithelium (RPE) layer or Bruch's membrane.

The image detecting unit may include an imaging beam irradiation unit which has a plurality of light sources for generating beams with different parameters and which is configured to irradiate the imaging beam, an imaging unit which is configured to collect the imaging beam which is irradiated by the imaging beam irradiation unit and reflected from the treatment region, and a processor configured to generate a fundus image based on a signal detected by the imaging unit.

The plurality of light sources may irradiate imaging beams corresponding to infrared light or visible light. At this point, the image detecting unit may acquire the fundus image by irradiating an imaging beam of a single wavelength or by simultaneously irradiating at least two imaging beams of different wavelengths.

The ophthalmic treatment device may further include a monitoring unit configured to irradiate a probe beam which travels along a path of the treatment beam, and detect information of a state of a location onto which the treatment beam is irradiated. During the irradiation of the treatment beam, the monitoring unit may irradiate the probe beam onto the location, onto which the treatment beam is irradiated, so as to detect the information of the state of the location.

The treatment beam generating unit may be controlled to irradiate the treatment beam onto a plurality of locations in the treatment region, and the image detecting unit may provide the user with information on locations onto which the treatment beam is irradiated.

The ophthalmic treatment device may further include an object part which is optically connected to the beam delivery unit and configured to provide a view of the treatment region to the user during treatment, and the display unit may be a display which is embedded in a slit lamp to allow the user to check the treatment region through the object part. At this point, the image detecting unit may acquire a fundus image using an imaging beam of a wavelength in an infrared light band.

The image detecting unit may irradiate an imaging beam to capture an image of fundus blood vessels to provide a user with information on oxygen saturation of fundus blood vessels.

Meanwhile, the aforementioned object of the present disclosure may be achieved by a method of operating an ophthalmic treatment device, the method including operating a treatment beam generating unit to irradiate a treatment beam onto a target location, operating a monitoring unit to irradiate a probe beam onto the location at which the treatment beam is irradiated, and collect the probe beam being reflected or scattered so as to detect information of a state of the location at which the treatment beam is irradiated, controlling operation of the treatment beam generating unit based on the detected information, acquiring, by an image detecting unit capable of adjusting a parameter of an imaging beam, a fundus image of an internal tissue in a treatment region including the target location, and displaying, by a display unit, the acquired fundus image.

According to the present disclosure, it is possible to perform treatment while checking information of the state of a patient's fundus tissue by using an image detecting unit. Therefore, it is possible to easily diagnose the patient's state and perform treatment while checking treatment procedures and whether treatment is complete at a specific location.

DESCRIPTION OF EXEMPLARY EMBODIMENTS

Hereinafter, an ophthalmic treatment device according to an embodiment of the present disclosure is described in detail with reference to accompanying drawings. In the following, location relationships between components are described based on the drawings. The drawings may illustrate the structure of the invention in a simple or exaggerated way, if necessary. Thus, aspects of the present disclosure are not limited thereto, and it is understood that other various devices may be added and that various modifications may be made.

In this embodiment, an ophthalmic treatment device for treatment of a fundus lesion is described as an example, but aspects of the present disclosure are not limited thereto, and the present disclosure can be applied to an ophthalmic treatment device for treatment of a lesion in areas other than the fundus.

Figure 1:
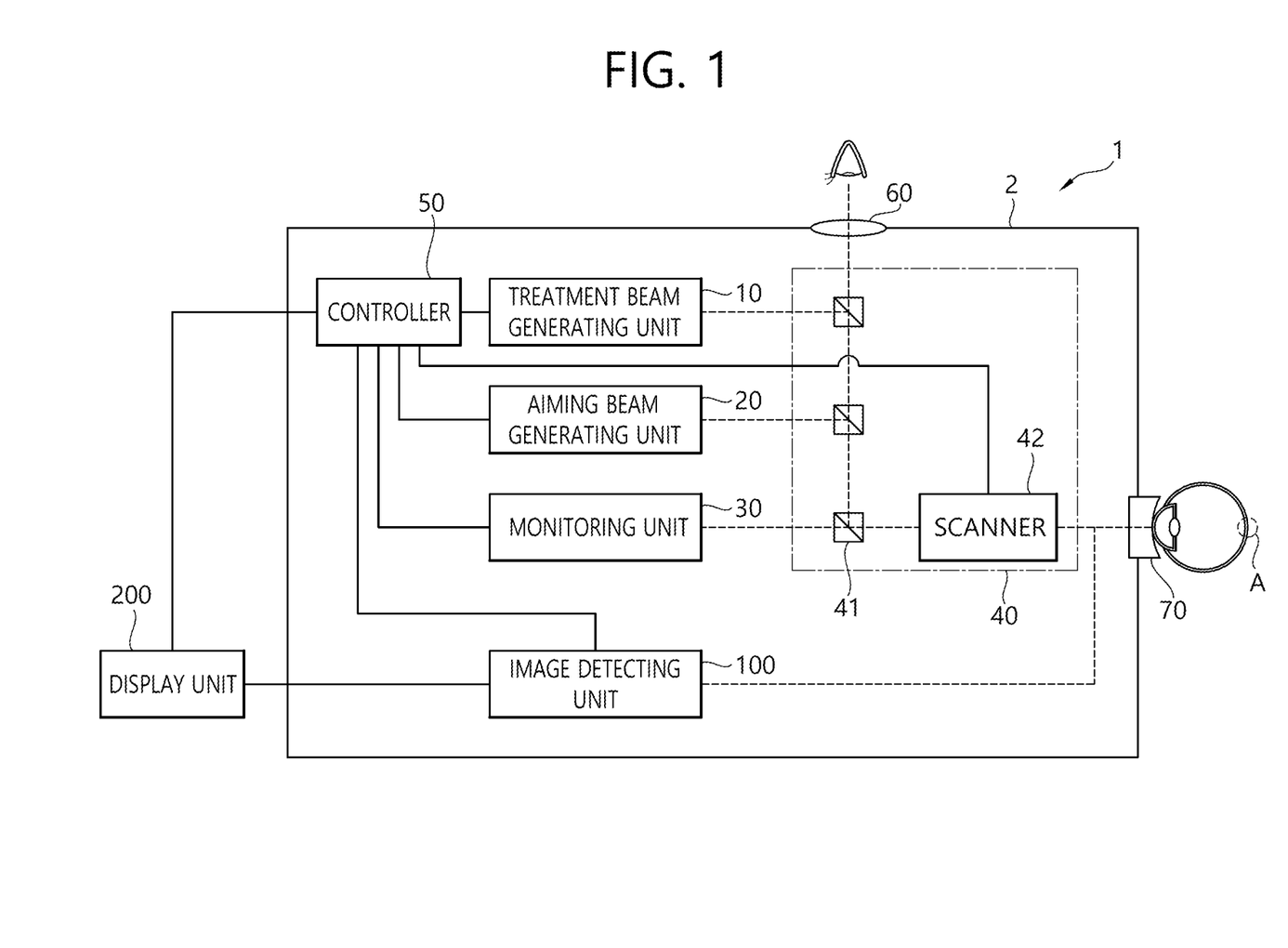
FIG. 1 is a schematic view illustrating an ophthalmic treatment device according to a first embodiment of the present disclosure.

FIG. 1 is a schematic view illustrating an ophthalmic treatment device according to a first embodiment of the present disclosure. An ophthalmic treatment device 1 according to the first embodiment may include a slit lamp 2. The slit lamp 2 may be used for treatment in which an object part 70 disposed on one side of the slit lamp is brought to a patient's eye, and a user is able to examine the patient's eye through an eyepiece part 60 disposed on the other side. Various components may be embedded in the slit lamp 2.

As illustrated in FIG. 1, the ophthalmic treatment device 1 includes a treatment beam generating unit 10 for generating a treatment beam, an aiming beam generating unit 20 for generating an aiming beam, and a beam delivery unit 40 for forming a path along which the treatment beam and the aiming beam travels to a treatment region. In addition, the ophthalmic treatment device may include a monitoring unit 30 for detecting information of the state of a location, at which the treatment beam is irradiated, during the treatment, and a controller 50 for controlling operation of the treatment beam generating unit based on the information detected by the monitoring unit.

The treatment beam generating unit 10 may include a treatment beam light source (not shown) for generating a treatment beam, and various optical devices for processing optical characteristics of the treatment beam generated by the treatment beam source. The treatment beam is in the form of laser, and the treatment beam light source may include a laser medium, such as Nd:YAG and Ho:YAG, or a laser diode which is capable of laser oscillation. In addition, the treatment beam generating unit 10 may include various devices, such as various electrical circuits for exciting laser, an optical filter for oscillating a light in a specific wavelength band, and a shutter.

The ophthalmic treatment device 1 according to the first embodiment is a device for treating various lesions, such as macular degeneration, which may occur in the fundus. A treatment beam is selectively provided to deliver energy to a specific target location or tissue. Thus, the ophthalmic treatment device 1 uses laser which is not absorbed well in other tissues and which has a wavelength or a pulse width that is selectively absorbed by a target tissue. The ophthalmic treatment device according to the first embodiment irradiates a treatment beam which is selectively absorbed in the Retinal Pigment Epithelium (RPE) layer from among multiple layers of retinal tissues.

Meanwhile, the aiming beam generating unit 20 is used to generate an aiming beam that is irradiated onto a treatment region. The aiming beam is used to inform a user of a location onto which a treatment beam is to be irradiated, before or during irradiation of the treatment beam, and the aiming beam is irradiated directly on the treatment region. The aiming beam has a wavelength in the visible light band, so that a practitioner can check the treatment region.

The aiming beam generated by the aiming beam generating unit 20 may be irradiated in the form of a single spot so as to indicate a location of one target location, or may be irradiated in the form of a plurality of spots so as to simultaneously indicate a plurality of locations at which the treatment beam is irradiated sequentially. In addition, the aiming beam may be irradiated in various ways: for example, the aiming beam may be irradiated in a lattice form or may indicate the boundary of a region onto which a treatment beam is irradiated.

FIG. 1 shows a case where the aiming light generating unit 20 irradiates an aiming beam through the beam delivery unit 40 along the same path as that of a treatment beam, but the aiming beam may travel along a different optical path. Besides, if a practitioner is able to check a target location of the treatment beam through an additional interface, the aiming beam generating unit may be omitted.

Meanwhile, the beam delivery unit 40 may include a plurality of optical devices disposed between the treatment beam generating unit 10 and the object part 70, and may form a optical path along which a treatment beam, an aiming beam, and/or a probe beam travels. The probe beam is irradiated by the monitoring unit and will be described later.

Specifically, as illustrated in FIG. 1, the beam delivery unit 40 includes a plurality of beam combiner 41. In this configuration, a treatment beam generated by the treatment beam generating unit 10, an aiming beam generated by the aiming beam generating unit 20, and a probe beam generated by the monitoring unit 30, which will be described later, may enter into the beam delivery unit 40 to travel along the same path and reach a target location. In addition, the aiming beam and the probe beam reflected from the target location may travel in the reverse direction along the path toward the eyepiece part 60 at which a user's eye is located, or may be incident on the monitoring unit 30.

The beam deliver unit 40 may include a scanner 42 which changes locations of irradiation of a treatment beam, an aiming beam, and a probe beam on the optical path. The scanner 42 may include at least one reflection mirror and a driver which rotates the reflection mirror. As the driver changes an angle of the reflection mirror that reflects a beam, a location of irradiation of each beam may be changed.

In addition, although not illustrated in detail in the drawing, the beam deliver 40 may further include more optical devices, such as a plurality of optical lenses or a plurality of optical filters, which condense or distribute beams.

In addition, the object part 70 is provided at an end of the beam delivery unit 40. The object part 70 is a part on which a patient's eye, a treatment object, is brought, and which may include a contact lens that comes in contact with the patient's eye. Besides, the object part 70 may further include a suction part which draws and fixes the patient's eye during the operation.

Figure 2:
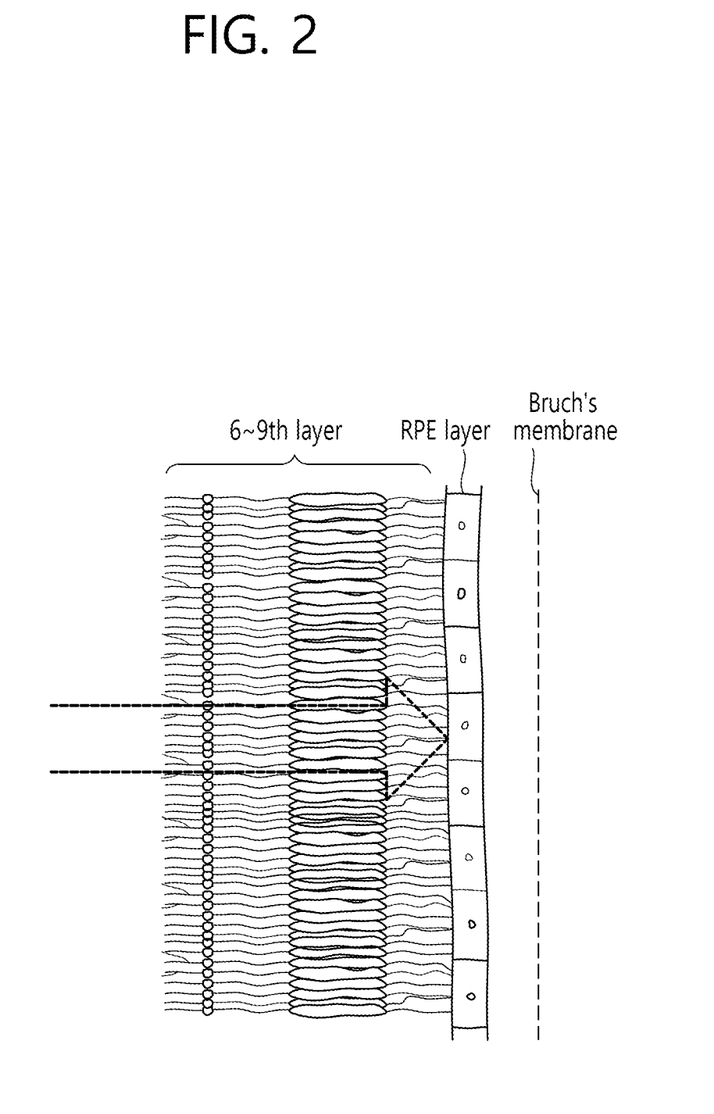
FIG. 2 is a cross-sectional view of an enlarged version of region A shown in FIG. 1.

FIG. 2 is a cross-sectional view of an enlarged version of region A shown in FIG. 1. FIG. 2 illustrates a diagram illustrating a patient's retinal tissue corresponding to a treatment region. The retina tissue consists of ten layers which include: an internal limiting layer, a nerve fiber layer, a ganglion cell layer, an inner plexiform layer, an inner nuclear layer, an outer plexiform layer, an outer nuclear layer, an external limiting layer, a photo receptor layer, a retinal pigment epithelial (RPE) layer (which are sequentially named in a direction from the retinal surface to the inside).

Among the ten layers, the RPE layer forms a boundary layer in the rear direction, and is in a tight junction structure. In addition, Bruch's membrane is positioned below the RPE layer. The RPE layer is supplied with nutrition and oxygen from blood vessels below Bruch's membrane and therefore supplies the nutrition to photo receptors. In addition, the RPE layer discharges wastes, generated by the photo receptors, through Bruch's membrane.

However, if some of RPE tissues of the RPE layer do not function properly, photo receptors positioned to correspond to those RPE tissues are not able to receive nutrition and oxygen properly, possibly being ended up with necrosis. Thus, the ophthalmic treatment device according to the first embodiment performs treatment in a manner of irradiating a treatment beam onto an improperly functioning RPE layer to provide energy to RPE tissues, so that new RPE tissues may be generated at locations onto which the treatment beam is irradiated.

More specifically, as described above, a treatment beam generated by the treatment beam generating unit 10 has a wavelength in a visible light band or an infrared light band. Such a wavelength is rarely absorbed by a tissue layer positioned at the front of retina (the first to ninth layers) and just passes through the layer. Then, the wavelength is absorbed by melanosomes which exist inside tissues of the RPE layer. Therefore, an amount of energy absorbed from the treatment beam is increased, the state of the RPE tissues is changed, and, in turn, new RPE tissues are generated. This may be because increase in temperature of the melanosomes causes occurrence of micro bubbles on the surface of the melanosomes, and the growing microbubbles can lead to necrosis of selective RPE tissues.

However, if an excessive amount of treatment beam is irradiated, it may cause heat damage not just to RPE tissues subject to the treatment, but adjacent RPE tissues or adjacent photo receptor tissues. Accordingly, this embodiment of the present disclosure may include a monitoring unit 30, as illustrated in FIG. 1, to monitor treatment procedures.

Specifically, when a treatment beam is being irradiated, the monitoring unit 30 may, in real time, monitor information of the state of a location, onto which a treatment beam is irradiated. Herein, the information of the state may include at least one of the following: information on change in temperature of tissues of the treatment region; information on change in volume of a tissue in the treatment region; information on change in an reflective index, information on movement of the tissue, or information on a signal that is generated accordingly. The monitoring unit 30 may be in various structures that enable detecting the information of the state of the treatment region.

For example, the monitoring unit 30 according to this embodiment may detect information of the state of a tissue based on photo interference information, as an optical coherent tomography (OCT) device does. Generally, an OCT device separates a single beam into a probe beam and a reference beam and transmits the two beams along different paths. If reflected from a target location, the probe beam is combined with the reference beam and collected. At this point, the OCT device acquires a CT image based on interference information of the two beams.

Just like the OCT device, the monitoring unit 30 according to this embodiment may provide different paths along which a probe beam and a reference beam travel. In this case, while the reference beam travels along a preset path, the probe beam is irradiated onto a target location along a path of a treatment beam through the beam delivery unit 40, and, once being reflected, the probe beam is collected by the monitoring unit 30. A detector of the monitoring unit may detect interference information which is about interference between the reference beam and the probe beam. Such configuration of the monitoring unit is similar to the configuration of the existing OCT device, and thus, detailed description thereof is omitted.

While the existing OCT device acquires a CT image by moving between coordinates in a horizontal direction (coordinates on a plane vertical to the path of a probe beam, B-scan), the monitoring unit 30 according to this embodiment irradiates a probe beam onto the same location multiple times during the treatment so as to detect change information of the state of a tissue in real time. Specifically, if a treatment beam is irradiated to deliver energy to a target location, characteristics of a tissue may be changed. As a result, this may change penetrating, scattering, and reflecting characteristics of the beam, and therefore, characteristics of the path of the probe beam are changed. Thus, if interference information detected by the monitoring unit 30 is changed, it is possible to detect that a state of the tissue is being changed by a treatment beam.

More specifically, in this embodiment, it is possible to extract information on depth of a target location from speckle pattern information that is acquired from interference information, and it is possible to continuously compare variation of the extracted information to detect a change in the state of the tissues.

However, the above-described configuration of the monitoring unit is merely exemplary, and the monitoring unit may be implemented in various ways. For example, the monitoring unit may be able to detect information on change in a state of tissues by employing an optical methods, such as a fundus camera, or may detect a signal which is generated by an acoustic wave sensor, an infrared sensor, a temperature sensor, etc. when a state of tissues is changed during irradiation of a treatment beam.

Meanwhile, the controller 50 controls the treatment beam generating unit 10, the aiming beam generating unit 20, the monitoring unit 30, the beam delivery unit 40, and the scanner 42. Thus, the controller 50 may control various components based on information input by a user or preset treatment information.

The controller may control operation of the treatment beam generating unit 10 based on information of the state of a target location, which is detected by the monitoring unit 30. Specifically, in order to treat a single target location, the controller 50 may control the treatment beam generating unit 10 to increase energy of a treatment beam. Once the monitoring unit 30 detects change in information of the state of the location, the controller may controls the energy of the treatment beam or stop irradiation of the treatment beam. In this manner, it is possible to prevent damage of adjacent tissues due to excessive irradiation of the treatment beam and to provide an appropriate amount of energy for optimal treatment.

Meanwhile, the ophthalmic treatment device 1 according to this embodiment of the present disclosure may further include an image detecting unit 100 and a display unit 200. The image detecting unit 100 captures an fundus image of a patient during treatment, and the display unit 200 displays the captured image for a user. Accordingly, the user is able to diagnose the state of the patient's fundus and check treatment procedures based on information of a treatment region shown in the image.

Figure 3:
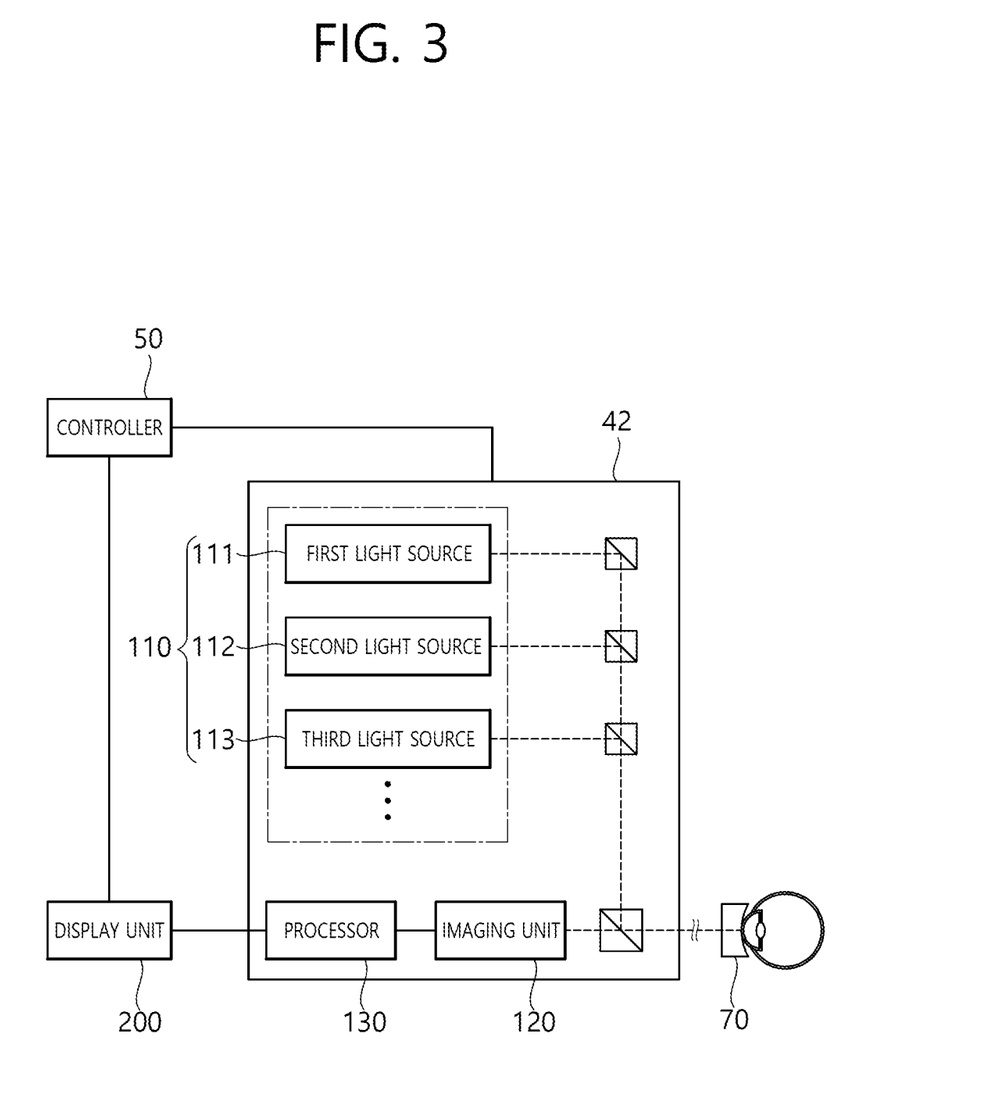
FIG. 3 is a block diagram illustrating configuration of an image detecting unit shown in FIG. 1.

FIG. 3 is a block diagram illustrating configuration of an image detecting unit shown in FIG. 1. As illustrated in FIG. 2, the image detecting unit 100 may include an imaging beam irradiation unit 110 for irradiating a beam onto a treatment region in the fundus, an imaging unit 120 for collecting an imaging beam reflected from the fundus, and a processor 130 for generating a fundus image based on information collected by the imaging unit 120.

As described above, the ophthalmic treatment device according to this embodiment is a treatment device for treating a lesion which occurs in the fundus. The fundus lesion is caused not by abnormality of a retinal surface tissue (the surface which can be seen through the pupil), but by abnormality of an internal tissue at the bottom of the retina, such as the RPE layer or Bruch's membrane (the tissue which is located deep to a certain point in the thickness direction of the retina and which cannot be seen on the surface of the retina). The treatment of the lesion is performed by targeting an internal tissue of the retina. Thus, in order to check the treatment procedures and diagnose a state of a patient's fundus, it is effective to acquire an image of the inside of retina, rather than an image of the surface thereof.

Therefore, the image detecting unit 100 according to an embodiment of the present disclosure may irradiate various types of imaging beams having different wavelengths. The depth by which a beam is able to penetrate into a tissue is different according to a wavelength of the beam. Thus, according to characteristics of a wavelength a beam, it is possible to acquire various images of tissue located at different depth from the surface of the treatment region. A practitioner may adjust the wavelength of an imaging beam to acquire an image of an internal tissue at a desired depth below a treatment region. Accordingly, based on the acquired image, the practitioner may be able to diagnose a state of the treatment region during the treatment, perceive treatment procedures, and check a treatment result after the treatment.

Specifically, the beam irradiation unit 110 may include a plurality of light sources 111, 112, and 113. A light source may utilize various devices capable of generating a beam, and, in this embodiment, the light source may utilize an Light Emitting Diode (LED) device which is excellent in selecting a wavelength.

In addition, the plurality of light sources may be configured to irradiate beams of different wavelengths. For example, the beam irradiation unit 110 may include n number of light sources, and, a first light source 111 may irradiate a beam of 300 mn wavelength, a second light source 112 may irradiate a beam of 400 mn wavelength, a light source 113 may irradiate a beam of 500 mn, . . . , and a n-th light source (now shown) may irradiate a beam of 1100 nm wavelength. In this embodiment, a wavelength of a beam may be selected from the infrared light band and the visible light band.

A beam irradiated from the beam irradiation unit 110 may travel along a path that is different from a path along which a treatment beam, an aiming beam, and a probe beam travel (see FIG. 1). According to this embodiment, the treatment beam, the aiming beam, and the probe beam travel to a target location on which treatment is to be performed, whereas an imaging beam may be irradiated to a wide area, which includes the target location and an area surrounding the target area, in order to acquire an image of a specific-sized area in the treatment region.

The imaging unit 120 collects an imaging beam reflected from the treatment region and generates a signal for acquiring an image. The imaging unit 120 may include a charge coupled device, such as a CCD and a CMOS. Although not illustrated in FIG. 3, the imaging unit 120 may further include a filter which is positioned at the front of the imaging unit 120 and selectively allows a beam of a specific wavelength to pass. A plurality of filters may be provided depending on a wavelength of an imaging beam. In addition, the filters may be able to move so as to be selectively disposed along a path of an imaging beam, irradiated from the imaging beam irradiation unit, according to a wavelength of the imaging beam.

The processor 130 may generate a fundus image based on a signal detected by the imaging unit 120, and deliver the generated fundus image to the display unit 200.

The image detecting unit 100 may acquire various types of fundus images under control of the controller. First of all, a fundus tissue layer to be captured and displayed for a user is determined based on the user's input signal or preset treatment description. Thus, the controller 50 selects a wavelength of an imaging beam based on depth of the corresponding tissue layer (the depth below the retinal surface) or a type of the tissue layer, and irradiates the imaging beam by operating a light source which corresponds to the wavelength among a plurality of light sources.

The imaging beam is irradiated onto the treatment region, travels into the depth of a desired tissue, is reflected from a portion adjacent to the desired tissue, and then is collected by the imaging unit 120. In this case, if necessary, the controller 50 may selectively operate a filter positioned at the front of the imaging unit so as to collect only a beam of a desired wavelength. The processor 130 composes a fundus image including an image of a desired internal tissue, based on a signal detected by the imaging unit 120. At this point, based on a signal received from the controller 50, the processor 130 may perform image processing, such as highlight an image of a specific inside tissue or removing an image of an unnecessary tissue.

At this point, the image detecting unit 100 may acquire a fundus image by using an imaging beam of a single wavelength, or may acquire a plurality of fundus images capturing different tissue layers by sequentially irradiating multiple imaging beams of different wavelengths.

Furthermore, it is possible to irradiate imaging beams of different wavelengths (e.g., simultaneously operating at least two light sources from among a plurality of light sources) so as to acquire fundus images in which a plurality of tissue layers at different depth overlap with each other. In the case of a spectral image captured by using multiple wavelengths, information of the state of the entire internal tissues of the retina, not information of the state of a specific location in the retina, may be shown in one fundus image. It is possible to acquire this kind of spectral image not just by simultaneously operating a plurality of light source, but by sequentially acquiring fundus images from the respective light sources and performing image processing on the acquired fundus images.

In this embodiment, the image detecting unit acquires an image of a location at a desired depth by considering the beam's characteristics of penetrating into a tissue by a different depth based on a wavelength thereof, but this is merely exemplary. Besides, it is possible to acquire an image of a desired depth by changing a different optical parameter that affects a beam's characteristic of penetrating into a tissue.

That is, in another embodiment, the plurality of light sources 111, 112, and 113, which are included in the imaging beam irradiation unit 110 of the image detecting unit 100, may irradiate beams having at least one different parameter that affects a beam's characteristics of penetrating into a tissue. The beam's characteristics of penetrating into a tissue may be changed by at least one of a polarization parameter, a phase parameter, and a wavefront parameter. Thus, the first light source 111, the second light source 112, and the third light source 113 of the imaging beam irradiation unit may irradiate imaging beams with at least one different parameter from among a polarization parameter, a phase parameter, and a wavefront parameter.

In this case, different images may be acquired using imaging beams irradiated from the respective light sources. Thus, it is possible to acquire an image by using a suitable light source, to selectively display a suitable image from among images acquired by the plurality of light sources, or to generate a suitable image by combine images acquired by the plurality of light sources and processing the combined image.

In the above, there is provided descriptions primarily about the characteristic that a beam penetrates a tissue by a different depth based on change of an optical parameter. However, according to constituent components, beams with different parameters may show different characteristics when it comes to penetration into a tissue, reflection from the tissue, or scattering. Thus, in the case of images acquired using a plurality of imaging beams of different optical parameters, different characteristics (e.g., tissue degeneration due to a lesion or treatment, a location of a blood vessel or a specific tissue, and tissue specificity of each person) are highlighted. Based on the above, it is possible to easily check characteristics of a tissue.

By doing so, the image detecting unit is able to acquire an image including fundus blood vessels and tissues, and information on oxygen saturation in consideration of advancing characteristics of an imaging beam according to oxygen saturation in the fundus blood vessels. Furthermore, based on these information, the imaging detecting unit is able to compute information on size of drugen in fundus.

Figure 8:
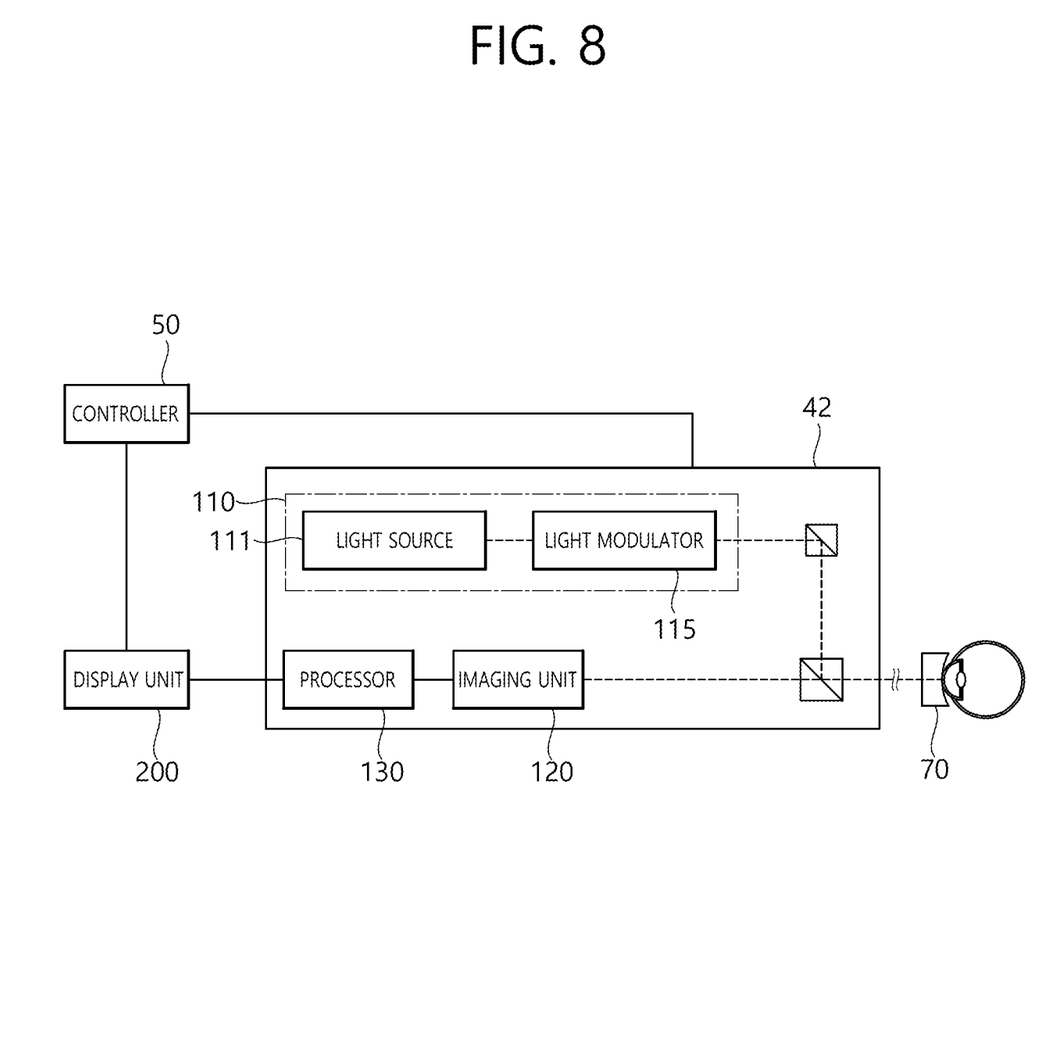
FIG. 8 is a block diagram illustrating another example of FIG. 3.

Meanwhile, this embodiment includes a plurality of imaging beam irradiation units to utilize various imaging beams, but aspects of the present disclosure are not limited thereto. In another embodiment, the imaging beam irradiation unit 110 may include a single light source 111 and a light modulator 115, as shown in FIG. 8. In addition, an imaging beam irradiated from the light source 111 may have a polarization, phase, or wave front parameter which is able to be modulated by the light modulator 115. In this case, the light modulator may be a polarization controlling member for controlling polarization of an imaging beam, a phase delay member for controlling phase of an imaging beam, and any one of various optical devices for controlling wavefront of an imaging beam. Accordingly, even when a single light source is used, various images may be acquired by adjusting parameters with the light modulator.

As such, the image detecting unit 100 may acquire a desired fundus image in various ways, and provide the acquired image to the display unit 200.

The display unit 200 displays a fundus image acquired by the image detecting unit 100 so that a user is able to see the image. The display unit 200 may be implemented using a device in various structures. In this embodiment, the display unit is provided as a display device, such as a monitor, which is provided separately from a slit lamp.

Figure 4:
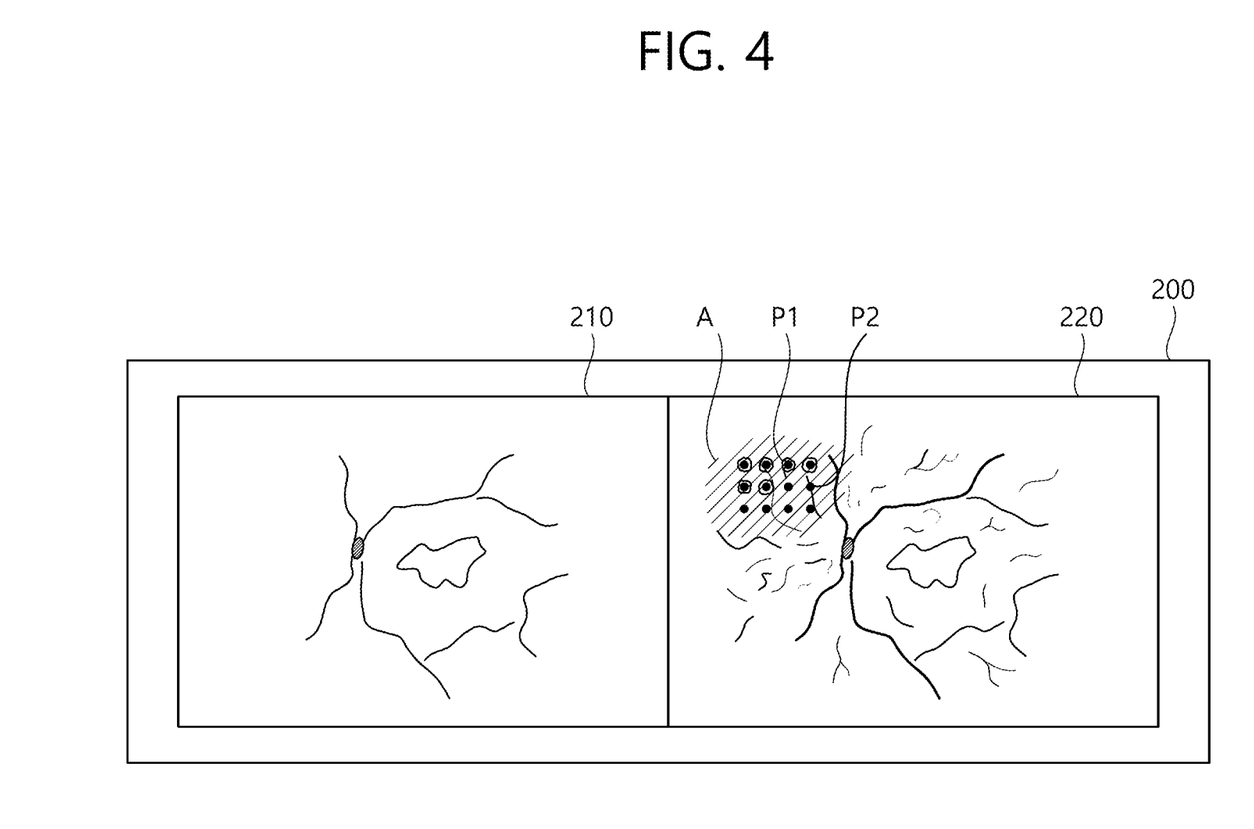
FIG. 4 is a front view of a display unit shown in FIG. 1.

FIG. 4 is a front view of a display unit shown in FIG. 1. As illustrated in FIG. 4, the left image 210 of the display unit 200 may be a fundus surface image which is acquired by a general fundus camera, and the right image 220 of the display unit 200 may be a fundus image which is acquired by the image detecting unit 100 and includes information of the state of an internal tissue.

The left fundus images 210 may be an image captured by a different diagnostic device, or may be an image of a retinal surface that is extracted by a processor from an image captured by the image detecting unit. Unlike the exemplary image shown in FIG. 4, the fundus surface image 210 may be omitted, or a fundus surface image and a fundus image including a fundus internal tissue may be selectively displayed.

The left fundus image 220 may show information on more details of a tissue located deeper inside the retina, compared to the left fundus image 210. For example, a fundus image acquired by using an imaging beam of 500 mn wavelength may highlights a tissue located at a first depth, whereas a fundus image acquired by using an imaging beam of 800 mn wavelength may highlight a tissue located at a second depth. Therefore, a user may perform a control operation to capture an image of a fundus tissue at a desired depth, and perform treatment based on the captured image.

Furthermore, the display unit 200 according to this embodiment of the present disclosure may set a location P1 in a lesion area shown in a fundus image, the location P1 at which a treatment beam is to be irradiated directly. Accordingly, the controller 50 may irradiate a treatment beam by controlling the treatment beam generating unit 10 and the beam delivery unit 40 based on information on a location of irradiation of the treatment beam set by a user. At this point, the display unit 200 provides the fundus image 220 of internal tissues of the treatment region so as to enable the user to check whether the treatment is being performed properly. For example, in FIG. 4, a treatment beam is irradiated onto six locations (P2) out of twelve locations (P1) onto which the treatment beam is set to be irradiated, and a change in the internal tissues of the retina is found.

Figure 5:
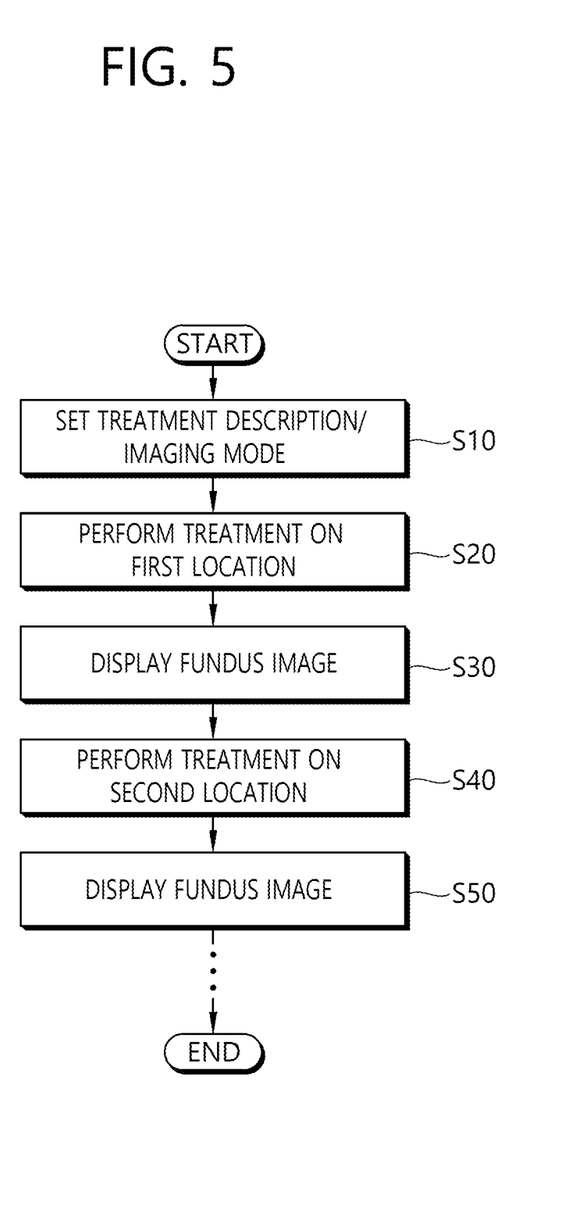
FIG. 5 is a block diagram illustrating a method of operating an ophthalmic treatment device shown in FIG. 1.
Figure 6:
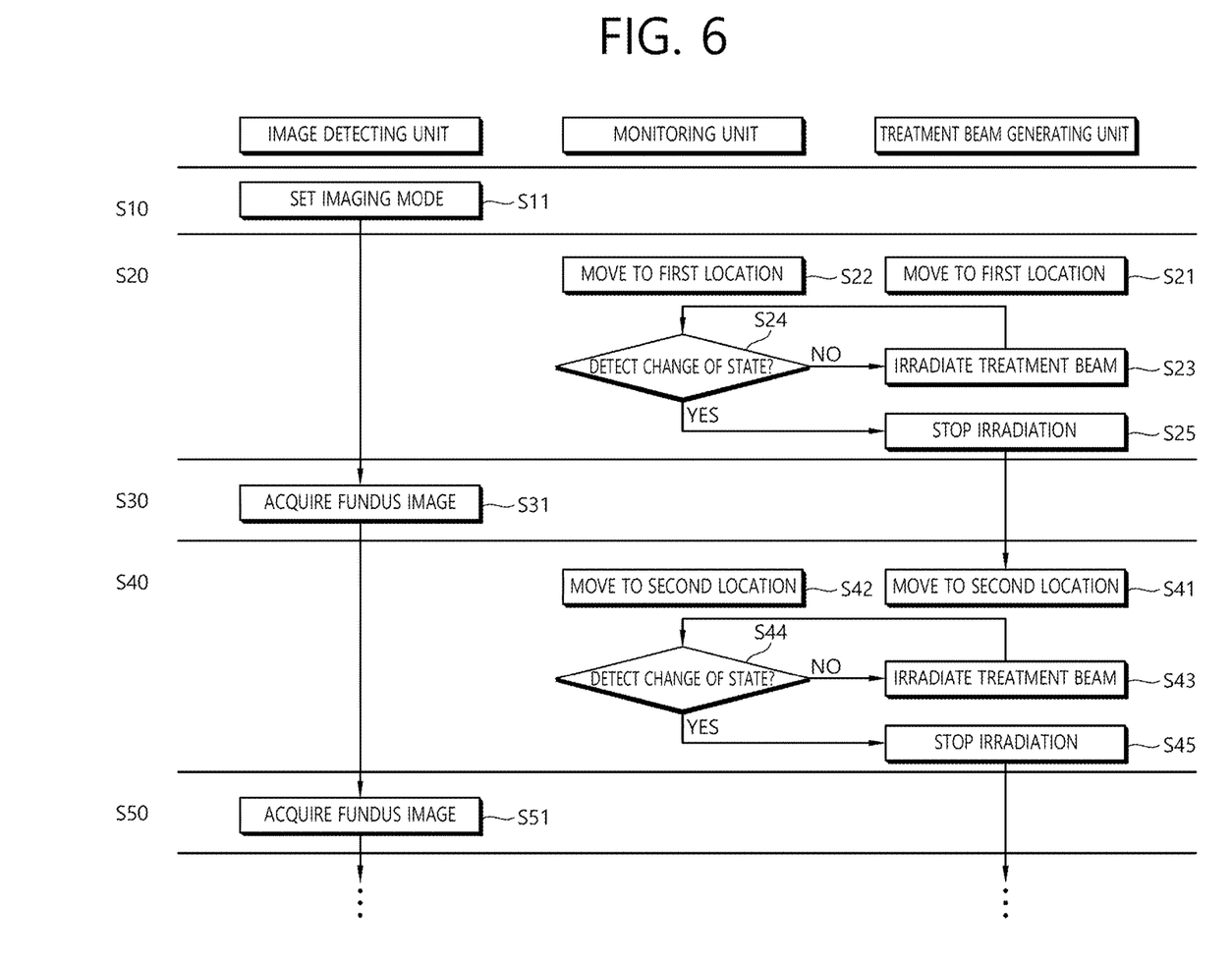
FIG. 6 is a block diagram illustrating how to operate each component according to the method shown in FIG. 5.

Hereinafter, specific examples of a method of operating an ophthalmic treatment device according to an embodiment of the present disclosure are described in detail. FIG. 5 is a block diagram illustrating a method of operating an ophthalmic treatment device shown in FIG. 1, and FIG. 6 is a block diagram illustrating how to operate each component according to the method shown in FIG. 5.

First of all, a user sets treatment description and an imaging mode based on a patient's lesion (S10). The treatment description may include a location of treatment, output of a treatment beam, and an irradiating pattern of the treatment beam. In addition, the imaging mode may include optical parameters of an imaging beam used to capture a fundus image, such as a wavelength of the imaging beam, and various operational conditions that can be adjusted to capture the fundus image. The treatment description and the imaging mode may be input by a user with a manipulating unit (not shown) or by selecting one of programmed modes.

Meanwhile, the treatment description may be set based on a diagnostic image acquired by an additional diagnostic device, or may be set based on a fundus image that is captured beforehand by an image detecting unit.

For example, to treat a patient having a macular degeneration lesion at a specific location, treatment description may be set to irradiate a treatment beam on a plurality of target locations so as to regenerate the RPE layers in the corresponding treatment region. In addition, an imaging beam may be set to have a wavelength suitable for capturing an image of tissues adjacent to the RPE layer or Bruch's membrane (S11).

Once the above step started, treatment may be performed at a first location from among a plurality of locations subject to irradiation of the treatment beam (S20). As illustrated in FIG. 6, the controller may operate a scanner of the beam delivery unit to aim a treatment beam and a probe beam at the first location (S21 and S22).

When the treatment beam and the probe beam aims at a specific location, the controller operates the treatment beam generating unit to irradiate the treatment beam (S23). In this step, the treatment beam, aiming at the first location, is irradiated multiple times in a pattern of increasing the output thereof.

In addition, when the treatment beam is being irradiated, the monitoring unit irradiates the probe beam onto the first location to detect any change in information of the state of the tissues (S24). The probe beam, aiming at the treatment beam, is irradiated multiple times so that it is possible to monitor a state of the tissues in real time. Accordingly, a state of the tissues is monitored each time of irradiation of the treatment beam, so that the treatment beam is controlled to be irradiated until any change of a state of the tissues is detected (S23). If any change of the state of tissues is detected, it may be determined that treatment of the first location is complete and thus the treatment may finish (S25).

When the treatment of the first location finished, a step for displaying fundus image is performed (S30). In this step, the image detecting unit acquires a fundus image based on a preset imaging mode (S31), and displays the acquired fundus image on the display unit. The fundus image displayed on the display unit shows information on tissues adjacent to the RPE layer or Bruch's membrane, so a user is able to check the treatment status and the treatment procedures based on the displayed fundus image.

Then, when the treatment of the first location finishes, a step of treating a second location proceeds (S40). The controller operates the beam delivery unit to aim a treatment beam and a probe beam at the second location, and performs treatment in the same manner that the first location was treated.

In addition, when the treatment of the second location finishes, a step of displaying a fundus image proceeds again (S50). At this point, as the location of irradiation of the treatment beam is changed, a probe beam is irradiated onto a different location by the monitoring unit, but the imaging detecting unit acquires an image of a specific part corresponding to the same treatment region.

Then, an operation of performing treatment on each location and an operation of displaying a fundus image may be performed repetitively.

In the above-described method, an image is displayed at a point when treatment of each location finishes. However, according to a pattern of irradiation of a treatment beam, an image may be acquired at a point when treatment of multiple locations finishes.

In another embodiment, the image detecting unit may not acquire an image at a specific location according to the above-described method, but may constantly acquire images in the course of treatment and display the acquired images in real time.

In addition, the above-described method enables a user to check an image of internal tissues during the treatment to check the treatment status and the treatment procedures. In another embodiment, an image may be acquired upon completion of the treatment so as to check whether a patient's lesion is treated through the treatment.

Figure 7:
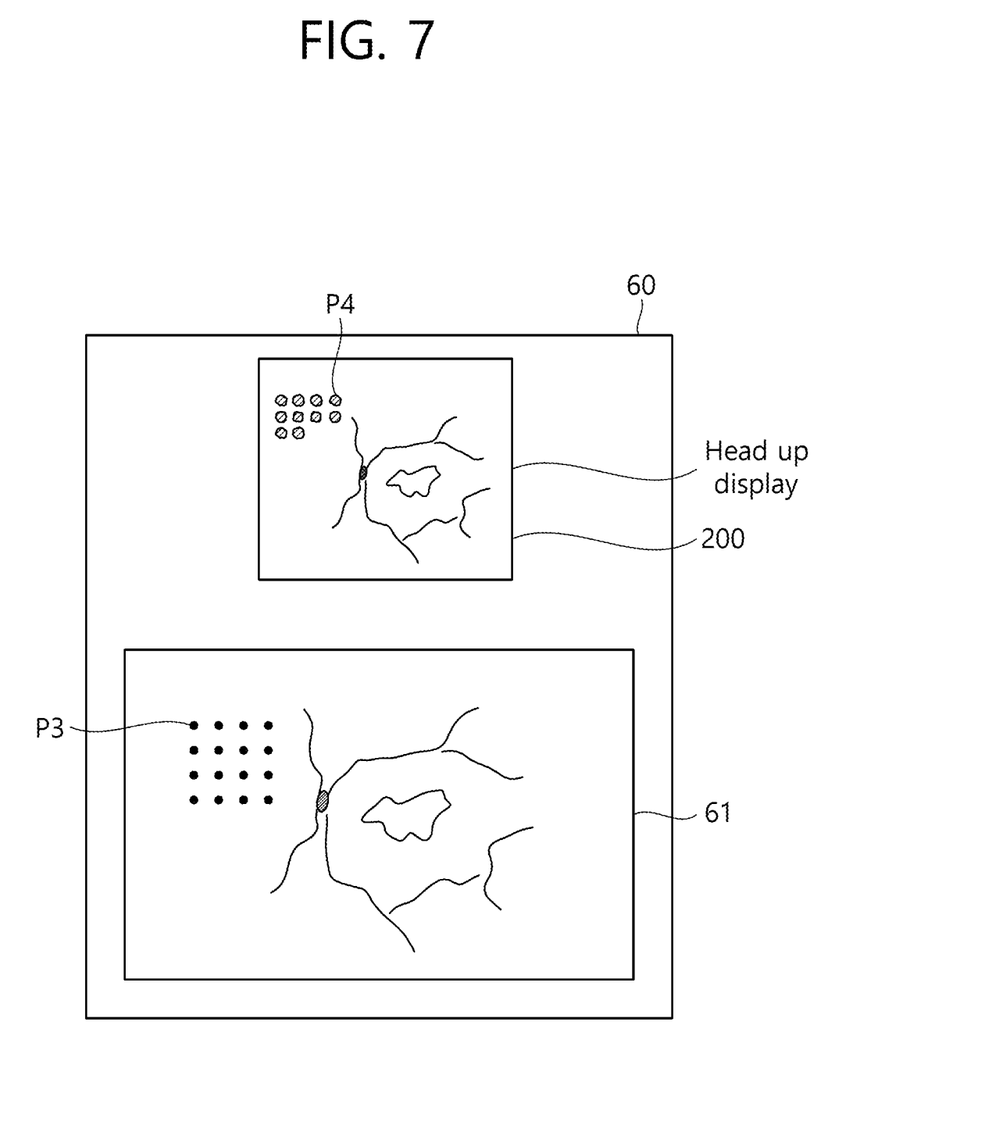
FIG. 7 is a diagram illustrating a display unit of an ophthalmic treatment device according to a second embodiment of the present disclosure.

FIG. 7 is a diagram illustrating a display unit of an ophthalmic treatment device according to a second embodiment of the present disclosure. Hereinafter, the ophthalmic treatment device according to the second embodiment of the present disclosure is described with reference to FIG. 7. Components corresponding to the components of the aforementioned embodiment are indicated with the same name and the same reference numeral, and description about other similar configuration or features is omitted to avoid repetition.

Similarly to the first embodiment, an ophthalmic treatment device 1 according to the second embodiment of the present disclosure includes a treatment beam generating unit 10, an aiming beam generating unit 20, a monitoring unit 30, an image detecting unit 100, and a display unit 200. Although the display unit in the first embodiment is exemplified as a display device provided separately from a slit lamp, the display unit in the second embodiment may be a display unit embedded in a slit lamp.

An object part 60 of a slit lamp 2 provides a view 61 to allow a user to check a patent's fundus along an optical path of the beam delivery unit 40. In addition, during the treatment, the user fixes his or her eyes onto the object part 60 to check the patient's fundus. Thus, as illustrated in FIG. 7, the display unit 200 according to the second embodiment may be embedded in the slit lamp 2 to be placed adjacent to the view 61 that is provided to the user through the object part 60. In this case, during the treatment, with fixing the eye onto the object part 60, the user is able to check information of the state of a tissue below the fundus, which is provided through the display unit 200.

Meanwhile, an image displayed on the display unit in FIG. 7 is a fundus image that is acquired using an imaging beam of a wavelength from among various image beams of different wavelengths.

As described with the above embodiment, the ophthalmic treatment device 1 according to the second embodiment performs treatment by irradiating a treatment beam onto a plurality of target locations on a treatment region. In this case, a target location at which the treatment beam is actually absorbed is a location adjacent to the RPE layer, so a user is not able to accurately distinguish a target location at which treatment is complete from a target location at which treatment is not yet complete, by observing the retinal surface through the view of the object part 60.

However, a beam of a wavelength in an infrared wavelength range is excellent in penetrating into tissues, and thus, if the beam of a wavelength in an infrared wavelength range is used, it is possible to reach a location at a desired depth, where the RPE layer or Bruch's membrane is positioned, and therefore acquire a fundus image including an image of a location adjacent to a corresponding tissue. At a time when treatment is complete, this kind of fundus image shows a location P4 at which the tissue adjacent to the RPE layer or Bruch's membrane changes in characteristics. Based on this fundus image, it is possible to identify a target location at which treatment is complete.

Therefore, even in a case where a patient moves the eyeball, the slit lamp is tipped, or a user pulls his or her eye back from the object part during the treatment in which a treatment beam is irradiated onto a plurality of locations, a target location at which the treatment is not yet complete may be identified based on a fundus image displayed on the display unit, and it is possible to prevent repetitive treatment on the same target location.

The method of operating the ophthalmic treatment device according to the second embodiment is the same as the method shown in FIGS. 4 and 5, and thus, detailed description thereof is omitted.

As described above, an ophthalmic treatment device is able to acquire an image of a fundus internal tissue, thereby improving user convenience and contributing to provision of optimal treatment. In particular, it is possible to select a wavelength of an imaging beam, so that images of different depth may be acquired and provided based on a user's demand and treatment description.

Although embodiments have been described with reference to a number of illustrative embodiments thereof, aspects of the present disclosure are not limited thereto. It should be understood that numerous other modifications and embodiments can be devised by those skilled in the art that will fall within the spirit and scope of the principles of this disclosure.

What is claimed is:

1. An ophthalmic treatment device comprising:
a treatment beam generating unit configured to generate a treatment beam;
a beam delivery unit configured to form a path along which the treatment beam generated by the treatment beam generating unit travels to a treatment region in fundus;
an imaging beam irradiation unit configured to generate an imaging beam;
an image detecting unit configured to adjust an optical parameter of the imaging beam that is irradiated onto an internal tissue of the treatment region so as to acquire a fundus image including the internal tissue; and
a display unit configured to display the fundus image, acquired by the image detecting unit, for a user,
wherein the image detecting unit adjusts a wavelength of the imaging beam based on a depth of the internal tissue below a surface of the treatment region.

2. The ophthalmic treatment device of claim 1, wherein the internal tissue is a tissue where the treatment beam is absorbed.

3. The ophthalmic treatment device of claim 1, wherein the internal tissue is away from a surface of a retina and adjacent to a Retina Pigment Epithelium (RPE) layer or Bruch's membrane.

4. The ophthalmic treatment device of claim 1, wherein the image detecting unit comprises:
the imaging beam irradiation unit having a plurality of light sources for generating beams with different parameters;
an imaging unit configured to collect a signal reflected from the treatment region; and
a processor configured to generate the fundus image based on the signal collected by the imaging unit.

5. The ophthalmic treatment device of claim 4, wherein the different parameters comprise different wavelengths.

6. The ophthalmic treatment device of claim 5, wherein the different wavelengths are for infrared light or visible light.

7. The ophthalmic treatment device of claim 4, wherein the imaging beam irradiation unit simultaneously generates at least two imaging beams with different parameters to acquire the fundus image.

8. The ophthalmic treatment device of claim 1, further comprising a monitoring unit configured to,
generate a probe beam which travels along a path of the treatment beam, and
detect information of a state of the treatment region,
wherein the monitoring unit irradiates the probe beam onto the treatment region, so as to detect the information of the state.

9. The ophthalmic treatment device of claim 1, wherein the treatment beam generating unit is controlled to irradiate the treatment beam onto a plurality of locations in the treatment region, and the image detecting unit provides the user with information on locations onto which the treatment beam is irradiated.

10. The ophthalmic treatment device of claim 9, further comprising an object part which is optically connected to the beam delivery unit and configured to provide a view of the treatment region to the user during treatment,
wherein the display unit is a display which is embedded in a slit lamp to allow the user to check the treatment region through the object part.

11. The ophthalmic treatment device of claim 9, wherein the image detecting unit acquires a fundus image using the imaging beam of a wavelength in an infrared light band.

12. The ophthalmic treatment device of claim 1, wherein the image detecting unit provides a user with information on oxygen saturation of fundus blood vessels.

13. A method of operating an ophthalmic treatment device, the method comprising:
operating a treatment beam generating unit to irradiate a treatment beam onto a target location;
operating a monitoring unit to irradiate a probe beam onto the target location, and collect the probe beam being reflected or scattered to detect information of a state of the target location;
controlling operation of the treatment beam generating unit based on the detected information;
acquiring, by an image detecting unit capable of adjusting a parameter of an imaging beam, a fundus image of an internal tissue in a treatment region including the target location; and
displaying, by a display unit, the acquired fundus image,
wherein the method further comprises selecting a wavelength of the imaging beam based on a depth of the fundus image below a surface of the treatment region.

14. The method of claim 13, wherein the acquiring of the fundus image comprises acquiring an image of a tissue adjacent to an Retinal Pigment Epithelium (RPE) layer or Bruch's membrane.

15. The method of claim 13, wherein the irradiating of the treatment beam comprises irradiating the treatment beam onto a plurality of locations in the treatment region,
wherein the acquired fundus image includes an image of the internal tissue whose state is changed by the irradiated treatment beam.

16. The method of claim 15, wherein the image detecting unit acquire the fundus image by using the imaging beam of a wavelength in an infrared light band.

17. The method of claim 13, wherein the acquired fundus image includes an image of a fundus vascular tissue.

* * * * *